United States Patent [19]

Papanek et al.

[11] 4,366,061

[45] Dec. 28, 1982

[54] AUTOMATED DIAPHRAGM APPARATUS AND METHOD FOR CONTROLLING NEGATIVE PRESSURE HEMODIALYSIS TREATMENT

[75] Inventors: Thomas H. Papanek, Oakland, Calif.; Mark S. Egler, Boston, Mass.; Julian I. Landau, Concord, Calif.

[73] Assignee: Cordis Dow Corp., Miami, Fla.

[21] Appl. No.: 203,075

[22] Filed: Oct. 31, 1980

Related U.S. Application Data

[63] Continuation of Ser. No. 114,776, Jan. 23, 1980, abandoned.

[51] Int. Cl.³ .................. B01D 31/00; B01D 13/00
[52] U.S. Cl. ............................ 210/647; 210/87; 210/96.2; 210/188; 210/321.3
[58] Field of Search ........... 210/85, 87, 96.2, 416.1, 210/321.3, 647, 188

[56] References Cited

U.S. PATENT DOCUMENTS 4,209,391 6/1980 Lipps et al. .................. 210/647

*Primary Examiner*—Frank A. Spear, Jr.
*Attorney, Agent, or Firm*—Neal A. Waldrop

[57] ABSTRACT

This invention provides an automated single pass dialysate supply apparatus and a method for conducting hemodialysis treatments when the apparatus is used. The apparatus is of the closed circuit type and provides a pair of cylinders, each equipped with a hydraulically driven diaphragm, which supply fresh dialysate to and remove spent dialysate from an artificial kidney on an alternating time basis; the improvement resides in the means which sense the difference in time of arrival of the end of stroke of each diaphragm and automatically counteract these differences to either maintain or restore synchronization of the instant of end of stroke of each diaphragm in each half cycle of operation.

The hemodialysis treatment method permits operator presetting of the desired ultrafiltrate removal rate and insures maintenance of that preset rate throughout the hemodialysis treatment period.

8 Claims, 14 Drawing Figures

FIG_3

FIG_7

FIG_8

FIG_9

FIG_10

FIG_11

FIG_12

AUTOMATED DIAPHRAGM APPARATUS AND METHOD FOR CONTROLLING NEGATIVE PRESSURE HEMODIALYSIS TREATMENT

This application is a continuation of application Ser. No. 114,776, filed Jan. 23, 1980, now abandoned.

BACKGROUND OF THE INVENTION

This invention relates to an improved single pass dialystate supply apparatus employing a pair of cylinders equipped with hydraulically driven diaphragms, and to a method for controlling the diaphragms and resultant dialysate flow to and from a hemodialyzer during hemodialysis. The apparatus of this invention is of the general type disclosed in copending application Ser. No. 958,329 now U.S. Pat. No. 4,209,391, entitled Apparatus and Method for Automatically Controlling Hemodialysis at a Pre-selected Ultrafilatration Rate which is assigned to the assignee of this application. The apparatus of this invention provides new means for providing flow of identical liquid volumes of dialysate to and from the kidney so as to attain the same general method of hemodialysis treatment that is achieved by copending application serial No. 958,329; the new means are modified and improved relative to the power driven pistons or diaphragms employed in that apparatus; the new means are also simpler and cheaper to manufacture and operate than the means of the prior disclosed apparatus.

The circuit of application Serial No. 958,329 employs a common power driven piston rod that is attached to pistons, or diaphragms, in each of two substantially equal volume cylinders. Oscillation of the piston rod causes dialysate to be supplied to and removed from a hemodialyzer on an alternating basis from one of the two cylinders while the other cylinder is being filled with fresh dialysate as spent dialystate in that same cylinder is being sent to drain. Heretofore, systems using a pair of matched volume output pumps have been commonly referred to as closed system and one such system is disclosed in U.S. Pat. No. 4,021,341. In the system of U.S. Pat. No. 4,021,341 the assumption is made that by employing inlet and output pumps operating at the same speeds, the volume of dialysate ot the kidney is the same as the volume of dialysate sent to drain and any excess volume in the line from the kidney represents water extracted from the blood in the kidney. This assumption has proved to be incorrect and systems relying on measurements of such excess fluid volume as the ultrafiltrate control mechanism have proved to be inaccurate and commercially unsatisfactory. The source of error in the equal volume assumption employed in connection with prior art closed systems was identified in application Ser. No. 958,329 and means were provided in its new circuit which solved the problem and eliminated the error in the false assumption by permitting only bubble-free dialysate to enter each of the two cylinders. As the result, the new circuit of application Serial No. 958,329 enabled control of ultrafiltrate rate merely by pre-setting the rate of bubble-free liquid withdrawn from the circuit through the use of an independently controlled ultrafiltrate withdrawal means such as a third piston or a volumetrically controllable pump.

The apparatus of this invention employs hydraulically driven diaphragms in lieu of the power driven pistons or diaphragms; the circuit of this invention is otherwise generally similar to that of Ser. No. 958,329. Early attempts to merely substitute hydraulic drives for positive mechanical drive in the diaphragm embodiment of that circuit were failures. It was found that flexible diaphragms passively driven in response to higher fluid pressure on one side of the diaphragm than on the opposite side faced an additional control problem due to fluctuations or variations in rate of traverse within the cylinder that were not encountered with positively driven diaphragms. It was observed that traverse rate fluctuations were variable with time and uncontrollable because the hydraulic driving pressure on the infeed dialysate was either the dialysate mixing pump pressure or water source line pressure and each such pressure is subject to unexpected variations; in contrast, the driving force in the spent dialysate line of the circuit is mechanically induced hydraulic pressure which results from pump operation that is likewise subject to sporadic variation. Summarily stated, it was found that the hydraulic driving force on the diaphragms in each of the two cylinder units for an entire cylinder length traverse was rarely, if ever, identical. These driving force variations cause the passively driven diaphragms in each of the cylinders to arrive at the end of stroke at different instants in time, with the absolute time difference varying as a function of the pressure variations during a given traverse from one side of the cylinder to the other. Whereas positive drive common to the two cylinders insured simultaneous attainment of end of stroke of the diaphragms in the fresh/drain and kidney/spent circuits, it became necessary with the hydraulically driven diaphragms to elect to switch valves at the instant of end of stroke of either the first or the second diaphragm. Attempts to switch at the instant of the first to arrival at end of stroke failed because of progressive shortening of each stroke; this procedure culminated in more and more rapid switching from cycle to cycle until final arrival in a flutter lock-up condition which is unsatisfactory. Switching at the instant of the second, or latest, end of stroke of the diaphragms in the two cylinders in the separate flow paths produces a no-flow condition of fluid in the circuit of the first to arrive diaphragm during the interim until the second diaphragm achieves its end of stroke.

It was found that when the no-flow condition occurred in the infeed, fresh dialysate supply line, undesirable effects resulted in the dialysate make-up portion of the single pass dialysate circuit which supplies the bubble-free fresh dialysate to the circuit of this invention. Alternatively, when the no-flow condition occurs in the spent dialysate removal line the flow of dialysate in the dialyzer is interrupted and diffusion rates across the semipermeable membrane are detrimentally affected. Based upon the undesirable aspects of these options it was found to be necessary to control the traverse of the diaphragms in each of the two cylinders such that the instant of end of stroke in each is synchronized.

The apparatus of this invention provides modified circuit elements and associated control means which achieve the necessary control of diaphragm traverse to attain the needed synchronization to enable successful commercial use of hydraulically driven diaphragms in hemodialysis treatments.

No more pertinent prior art to this invention is known than that discussed in the specification of application Ser. No. 958,329 and that disclosure is hereby incorporated into this specification. An automated two constant volume displacement pump system for supplying dialysate to and from a hemodialyzer is disclosed in U.S. Pat. No. 4,113,614. In that system the assumption of equal pumped volumes to and from the hemodialyzer is relied upon and is erroneous and inaccurate because of failure to remove bubbles from the spent dialysate prior to arrival at the dialysate effluent pump. Additionally, one embodiment of U.S. Pat. No. 4,113,614 employs a dialyzer having filtration characteristics that are not constant and known and to establish a near constant ultrafiltration rate in that embodiment presets a transmembrane pressure and during hemodialysis measures the quantity of fluid in excess of that pumped out as effluent and automatically adjusts the transmembrane pressure in response to variations in rate of ultrafiltrate generation. In comparison, the present invention does not preset transmembrane pressure, but does preset ultrafiltrate withdrawal rate.

A second embodiment of U.S. Pat. No. 4,113,614 employs a dialyzer having filtration characteristics that are constant and known; in this embodiment ultrafiltration rate is preset and the quantity of fluid in excess of that pumped out as effluent is measured and differences in the rate of ultrafiltrate generation are used to generate signals which control the pressure in the system. In contrast, this invention uses a hemodialyzer having filtration characteristics that are not constant. This invention makes no attempt to control pressure in the system and relies upon fluid withdrawal to produce inherent pressure conditions to generate from the blood the quantity of water that equals the withdrawn quantity of dialysate; this invention maintains the hydraulic integrity of the entire circuit by insuring that the precise quantity of bubble-free dialysate fed to the kidney does equal the quantity of bubble-free dialysate that is sent to drain, and withdraws only bubble-free ultrafiltrate. Moreover, and as above mentioned to avoid dialysate make-up undesirable effects or irregular flow rates through the kidney, this invention monitors fluid flow rates in the fresh/drain and in the kidney/spent circuits and employs the difference in time of arrival of each of the diaphragms in the two cylinders at its end of stroke to generate signals that in turn are used to change the rate of dialysate flow in the spent dialysate removal line to thereby synchronize the end of stroke instant for the two diaphragms.

SUMMARY DESCRIPTION OF THIS INVENTION

This invention departs from the prior art, and the apparatus described and claimed in the above described circuit of application Ser. No. 958,329 primarily because of the discovery that the hydraulically driven diaphragms in the circuit of this invention must be synchronized in such a manner so as to complete their traverse in each cylinder in each half cycle in the same direction of movement at the same instant in time. "Half-cycle" hereinafter and in the claims refers to traverse of the diaphragm between the ends, or sides, of a cylinder in a single direction. Such synchronization overcomes and offsets or compensates for any variation in driving force on each diaphragm in its cylinder. Each diaphragm functions alternately in the fresh/drain or kidney/spent circuit such that at any given instant in time each diaphragm is monitoring the flow rate in a circuit isolated from the circuit of the other diaphragm. Due to this circuit isolation it is unnecessary that the time interval for each half-cycle be identical; it is also unnecessary that the cylinder volumes be identical. It is, however, desirable that the flow rate during one half-cycle be substantially the same as the flow rate during the other half-cycle. Thus, it is desirable that the cylinder volumes be substantially the same, for example, within ±5%.

the new apparatus is modified to include flow measuring means, or switches, in the infeed, fresh bubble-free dialysate line and also in the spent dialysate removal line. These flow switches detect end of stroke of the diaphragms in each circuit and feed an electrical signal to a microprocessor which feeds corrective signals to the pump in the spent dialysate removel line on the following, or next delayed, half-cycle to correct flow rate of the spent dialysate so as to bring about synchronization of the instant of end of stroke in each diaphragm in each half-cycle on a continuing, or continuous, basis. The system also includes a pressure transducer in the spent dialysate removal line, as shown, which detects pressure changes in the spent dialysate caused by patient blood pressure, kidney permeability changes, operator change of ultrafiltrate withdrawal rate, etc., and feeds signals to the microprocessor which, in turn, feeds corrective signals to the pump in the spent dialysate line to restore the rate of flow to its rate prior to any change due to the detected pressure change.

DETAILED DESCRIPTION OF THE PREFERRED APPARATUS EMBODIMENTS

Figure 1:
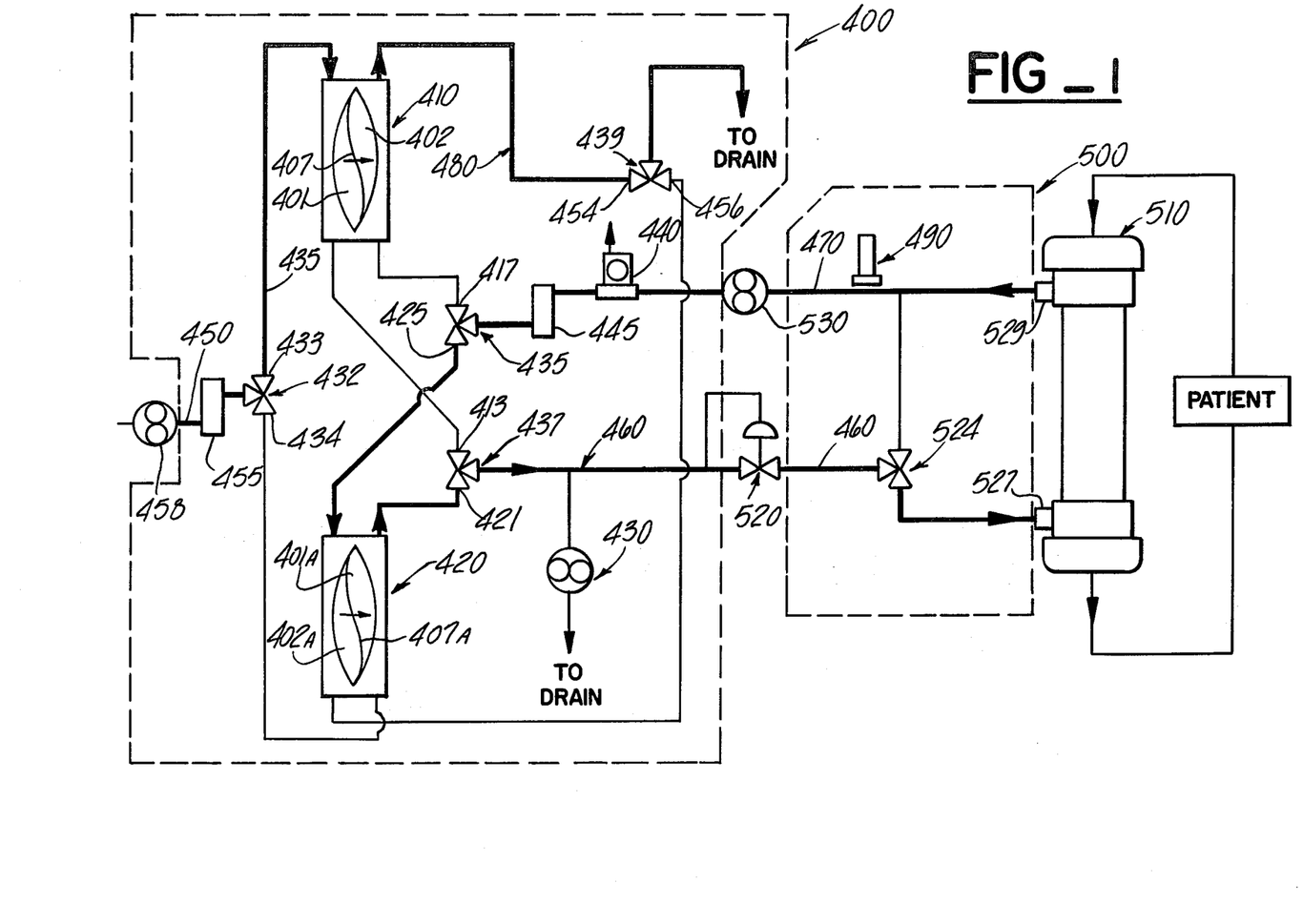
FIG. 1 is a schematic illustation of the improved circuit of this invention showing the dialysate flow path of each cylinder when the switching valves are in valve state A in heavy lines.
Figure 2:
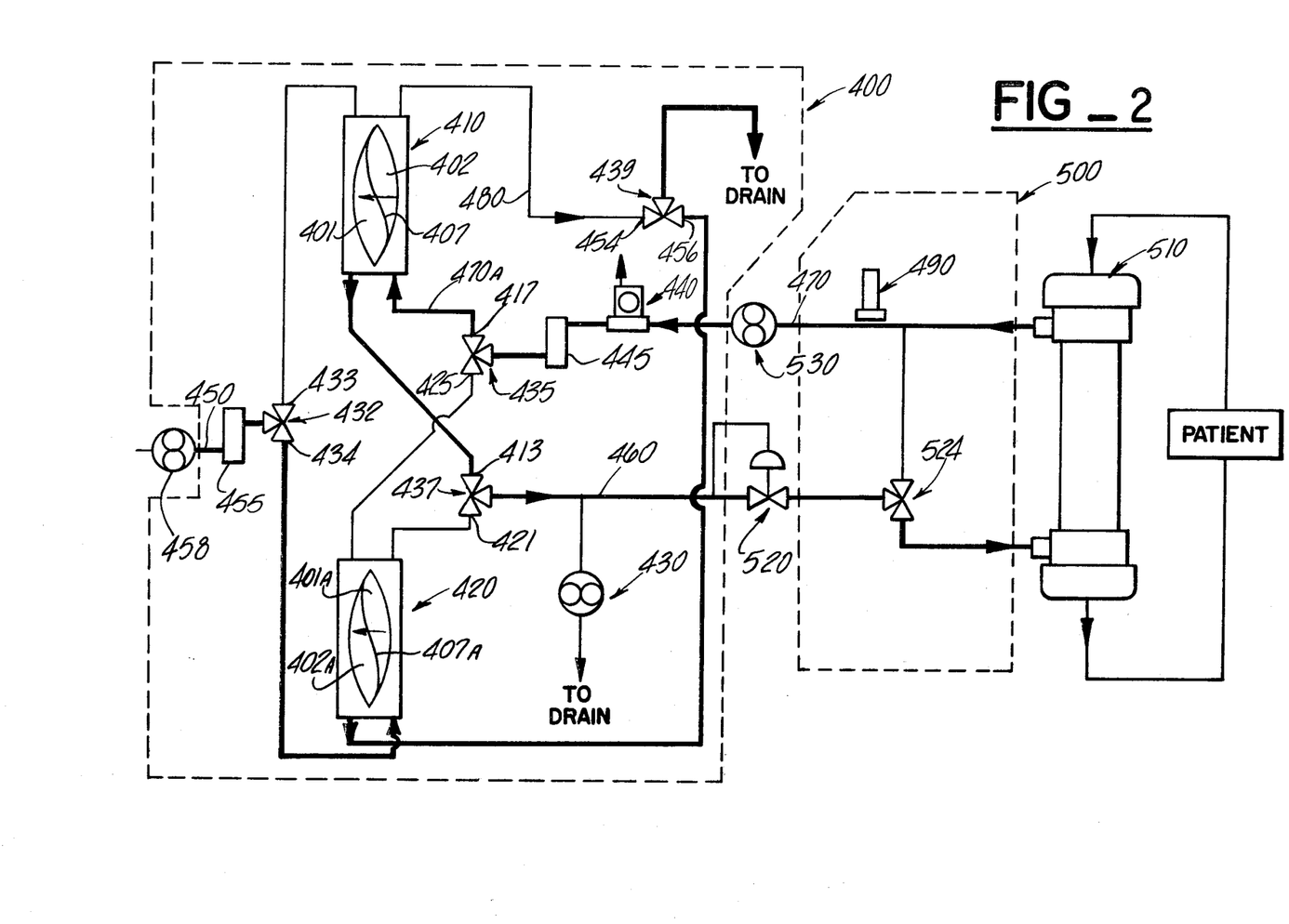
FIG. 2 is a schematic illustration similar to FIG. 1 showing, in heavy lines, the dialysate flow path of each cylinder when the switching valves are in valve state B.

As may be seen in the FIGS. 1 and 2 the circuit of this invention comprises an above atmospheric pressure portion which includes those elements circumscribed by the dash line generally designated 400 and a below atmospheric pressure portion containing the elements enclosed by the dash line area generally designated 500. The functional components, or elements, of the circuit which remain at all times above atmospheric pressure include cylinder units 410 and 420, upstream fresh dialysate flow-inducing means 458, inlet dialysate flow detecting means 455, and valves 432, 435, 437 and 439 as shown in FIG. 1 and FIG. 2, ultrafiltrate removal means or metering pump 430, degasifier 440 and spent dialysate removal line flow detecting means, or switch, 445. The components in the below atmospheric pressure portion 500 include the dialysate chamber portion of the hemodialyzer generally designated 510 and the optionally present dialysate detector means 490. The main components between the above atmospheric pressure portion 400 and the below atmospheric pressure portion 500 are the pressure reducing means generally designated 520, and spent dialysate flow generating, or pump, means generally designated 530. Spent dialysate pressure detector means 490 when optionally present satisfactorily is located in either the fresh dialysate line 460 or preferably is located in the spent dialysate line 470, as shown. Hemodialyzer 510 may be any of the commerical types but preferably the semipermeable membranes are hollow fibers.

The above identified functional and main components in the above and below atmospheric pressure portions, respectively, are interconnected in the closed hydraulic circuits shown in FIG. 1 which corresponds to valve state A, and in FIG. 2, which corresponds to valve state B, on an alternating time basis during use. Taken collectively the circuits of FIGS. 1 and 2 provide a continuous supply of fresh dialysate to and remove spent dialysate from artificial kidney 510 and enables a set ultrafiltrate withdrawal rate to cause the withdrawal of bubble-free ultrafiltrate, or water, to be extracted from the blood; the set ultrafiltrate withdrawal rate constitutes the control parameter which instantaneously and continuously induces pressure changes between the blood flowing on one side of the semipermeable membrane in the kidney and the dialysate flowing on the other side of that membrane to cause the desired quantity of water to be so removed at the desired rate of such removal. This mode of operation is generally similar to that of Ser. No. 958,329, but differs therefrom in specifics and on an instantaneous basis consequent from the use in the dialysate cylinders 410 and 420 of passively driven diaphragms as opposed to power driven pistons or diaphragms.

The functional relationships between the elements in the circuits as interconnected during alternating half-cycles of dialysate flow will, for simplicity, be explained with specific reference to the state of the valve generally designated 432 in incoming fresh dialysate supply line 450 under the designations valve state A and valve state B. Valve state A is illustrated in FIG. 1 wherein dialysate flow is indicated by the heavy lines in the directions of the arrows thereon. Valve state B is illustrated in a similar manner in FIG. 2.

During valve state A, FIG. 1, port 433 is open and port 434 is closed; during this half-cycle fresh dialysate flows through supply line 450, through flow detecting means 455, through open port 433 and line 435 into chamber 401 of cylinder 410. Fresh dialysate is supplied through line 450 in premixed bubble-free form and typically at 37° C. and under a positive pressure of about 2 to about 10 pounds per square inch. The positive pressure at valve 432 provides the propelling force for the dialysate in the fresh/drain circuit and may be produced, or controlled, by pump 458, or equivalent means such as a pressure regulator, not shown, or by other flow inducing means located in an upstream dialysate generating circuit of the type, for example, as that shown in copending application Ser. No. 927,322 which is owned by the assignee of this application, the disclosure of which is hereby incorporated in this application.

In valve state A the inflow of dialysate into chamber 401 causes hydraulically driven diaphragm 407 to move to the right, in the direction of the arrow, and to expel from chamber 402 spent dialysate through line 480 and through port 454 of valve 439 to drain. Thus, during valve state A, cylinder 410 performs the functions of receiving fresh dialysate and sending spent, or effluent, dialysate to drain and the circuit performing these functions will hereinafter be designated the fresh/drain circuit. During this same time elapse in the valve state A half-cycle, fresh dialysate is supplied to kidney 510 from chamber 401A of cylinder 420 and spent dialysate is received from kidney 510 in chamber 402A; it is to be understood that all valves in the circuits, except by-pass valve 524, operate to open or close at substantially the same instant in time such that dialysate flow remains substantially constant to and from kidney 510 at all times, that while cylinder 410 is filling with fresh dialysate, cylinder 420 is filling with spent dialysate and that during the succeeding half-cycle the cylinder functions reverse. The driving force for spent dialysate flow in spent dialysate line 470 is power driven means 530, usually a pump which satisfactorily may be a positive displacement pump, or preferably is a more inexpensive pump such as a gear pump. The control of rate of flow of spent dialysate through detection of the instant of end of stroke of the passive diaphragms in cylinders 410 and 420 is important and will be explained hereinafter in greater detail in connection with the automated control modifications and method of operation. As pump means 530 propels spent dialysate from outlet port 529 in kidney 510 through bubble removal means 440, and flow rate detector 445, through open port 425 of valve 435 into chamber 402A of cylinder 420, passive diaphragm 407A is forced to move to the right, in the direction of the arrow, and to expel the fresh dialysate in chamber 401A, through open port 421 of valve 437 along line 460 through pressure reducing means 520 to the inlet port 527 of kidney 510. Thus during valve state A cylinder 420 performs the functions of sending bubble-free fresh dialysate to the kidney and receiving spent dialysate from the kidney and the circuit performing these functions will hereinafter be designated the kidney/spent circuit. It should be noted that during the valve state A half-cycle, both hydraulically driven diaphragms 407, 407A move in the same direction and physically reach the right hand end of cylinders 410 and 420 at approximately the same instant in time, with specific variance being a function of varying dialysate rates of flow in the two cylinders, as above generally stated.

Referring now to FIG. 2, the interconnection between the elements in the circuit in valve state B is illustrated. The reversal of functions of cylinders 410 and 420 results from the new interconnections of the circuit elements when ports 433, 454 are closed and ports 434 and 456 are simultaneously opened. By these valve changes fresh dialysate is shunted to cylinder 420; at the same instant valves 437 and 435 are reversed thereby shunting spent dialysate to cylinder 410 through line 470A as fresh dialysate is forwarded to kidney 510 through line 460. By referring to the heavy lines in FIG. 2 it may be seen that cylinder 410 is operatively connected into the kidney/spent circuit while cylinder 420 is connected into the fresh/drain circuit. It may also be seen that both of diaphragms 407, 407A move in the direction of the arrows, toward the left during the valve state B half-cycle and arrive at their end of stroke at the left hand end, or side, of their respective cylinders 410 and 420.

In each of the circuits shown in FIGS. 1 and 2 ultrafiltrate withdrawal means generally designated 430 is interconnected between drain and, as shown, fresh dialysate supply line 460 at a location within the above atmospheric pressure portion 400. However, ultrafiltrate withdrawal, or metering, means 430 satisfactorily may be connected between line 470 and drain at any other point between bubble removal means 440 and valve 435.

Figure 4:
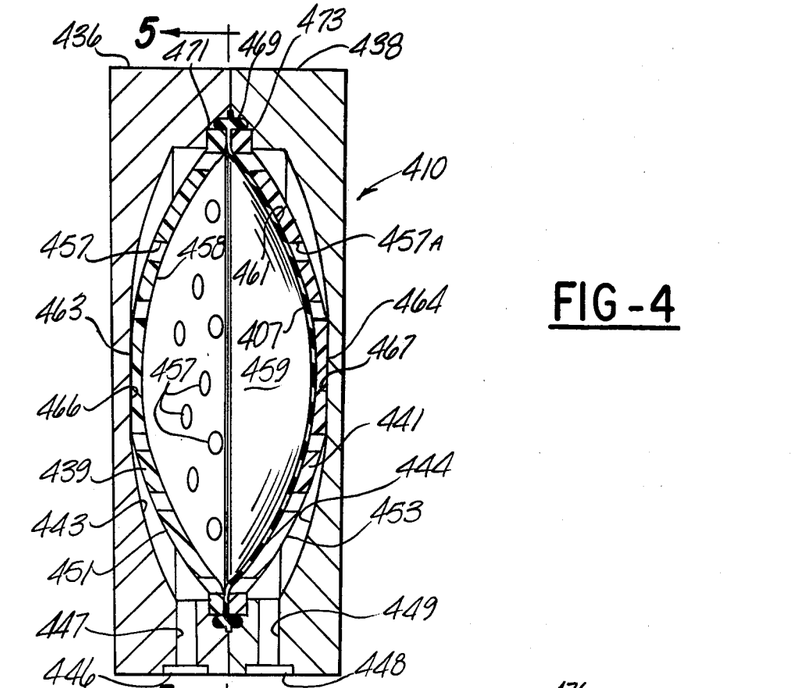
FIG. 4 is a vertical cross-section of one of the cylinder assemblies used in the circuit of this invention showing the hydraulically driven diaphragm in its end of stroke position on the right hand side of the cylinder.
Figure 5:
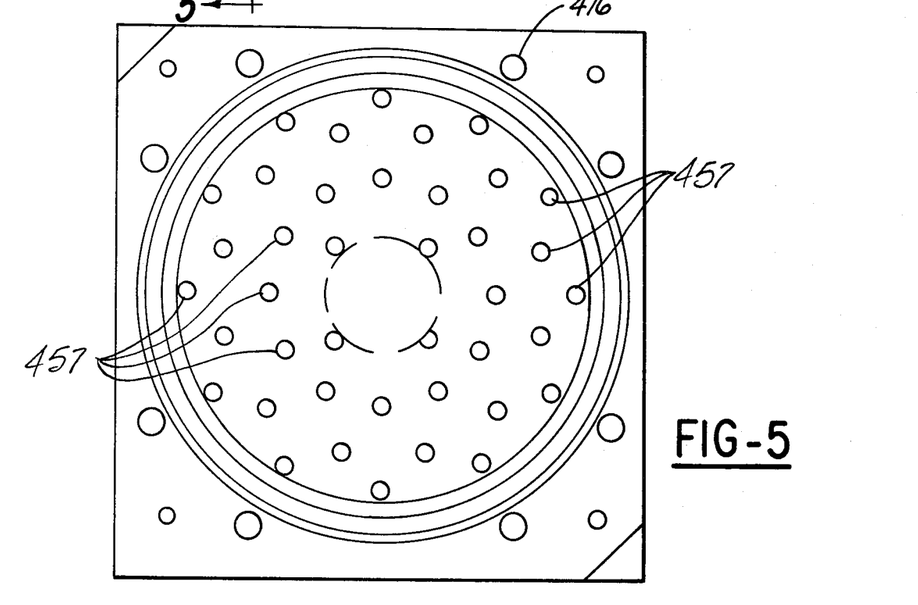
FIG. 5 is an elevation view of a disassembled half of the cylinder assembly of FIG. 4 looking toward the left half and showing the distribution of the dialysate flow path openings in the diaphragm support member.
Figure 6:
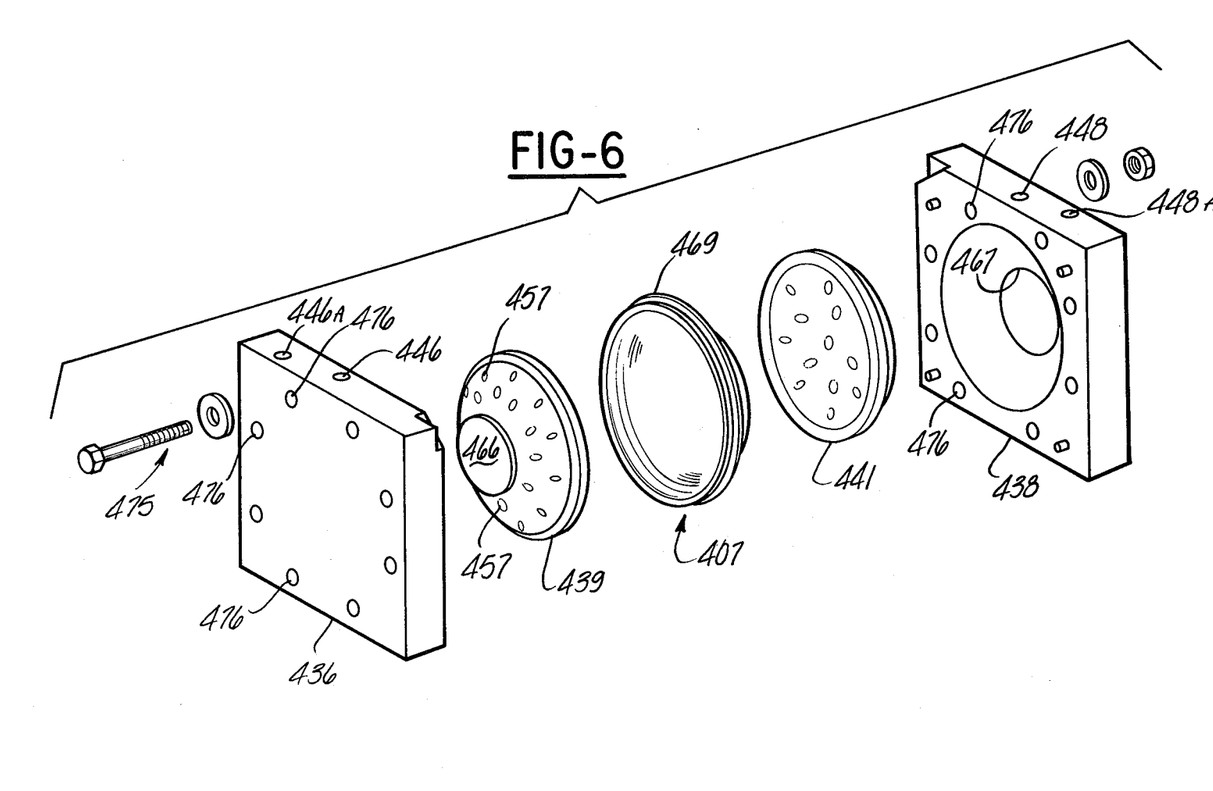
FIG. 6 is an exploded view of the disassembled parts of the cylinder assembly of FIGS. 4 and 5.

Dialysate cylinder units 410 and 420 which are schematically shown in FIGS. 1 and 2 are similar in construction and are illustrated in greater detail in their preferred form in FIGS. 4, 5 and 6. Referring to FIG. 4 and with specific reference to cylinder 410, diaphragm 407 is shown in its end of stroke position on the right hand side of cylinder 410. Cylinder unit 410 is an integrated assembly consisting of two mirror-image end plates 436, 438, a first diaphragm support member 439 for assembly into left hand end plate 436, a second diaphragm support member 441 for assembly into right hand end plate 438, and diaphragm 407. End plate 436 is provided with a generally hemispherical shape dished out recess chamber 443 which interconnects with outlet port 446 through channel 447 and with an inlet port 446A. In a similar manner, end plate 438 is provided with a similar shape recess chamber 444 which interconnects with outlet port 448 through channel 449 and an inlet port 448A. Ports 446, 448 as shown in FIG. 4 are shown on the lower end surface of plates 436, 438 but are preferably located on the upper, or top edge surface of end plates 436, 438 when physically installed for use in the circuit to thereby insure avoidance of gas bubble entrapment during start up of operation, or the like. Each chamber 443, 444 is provided with a centrally located circular support surface 463, 464 which receives a mating projection, or boss 466, 467 extending outwardly from the rear surface of each support member 439, 441, respectively to counteract pressure forces on diaphragm 407 at end of stroke.

Each diaphragm support member, or plate, 439, 441 is dish shaped at a selected non-hemispherical curvature adapted to produce upon assembly the desired cavity between the rear wall, surfaces 451, 453 of plates 439, 441, respectively, and the inner surfaces of the chambers 443, 444 in end plates 436, 438, respectively. Each support member 439, 441 is provided with a plurality of radially and circumferentially spaced apertures 457, 457A which extend through the wall of each support member and provide a flow path for dialysate, or other liquid between the central cavity 459 of oblate shape defined by the inner walls 458, 461 of support members 439, 441, respectively and the cavity in communication with it as diaphragm 407 moves from one side of cavity 459 to the other during traverse in alternate valve states A and B. As shown in FIG. 4, diaphragm 407 is in position at the end of stroke of valve state A, FIG. 1, and was forced to the right by dialysate fluid entering chamber 443 through an inlet port 446A, as that dialysate flowed through apertures 457 and exerted pressure on the left hand surface of diaphragm 407 in excess of the fluid pressure on the other side of the diaphragm to thereby cause dialysate flow through apertures 457A into chamber 444 and exit to drain through port 448. It will be seen that diaphragm 407 serves as a closure valve for each aperture 457A in support member 441, and as that flexible diaphragm moves into contact with inner wall 461 all fluid is expelled into chamber 444 due to the distribution of such apertures over the entire surface of inner wall 461. Support members 439, 441 serve the further function of preventing malfunction in full diaphragm traverse and consequent failure to expel in each half cycle all of the dialysate received during the immediately prior half-cycle.

Diaphragm 407 is satisfactorily fabricated from any thin, flexible resilient sheet material such as rubber, or plastic materials and is secured and hydraulically sealed between end plates 436 and 438 by peripheral bead 469 which is wedged between and overlies the peripheral edge of the flanges 471 and 473 of support members 439 and 441, respectively, as shown. As best seen in FIG. 6, cylinder 410 is assembled by first positioning support members 439, 441 in their end plates 436, 438, respectively. Diaphragm 407 is then placed into position and the parts are unified by a plurality of fasteners, such as the illustrated bolt, washer and nut generally designated 475, positioned and tightened in circumferentially spaced apertures 476 in members 439, 441.

AUTOMATED METHOD OF OPERATION OF THE CIRCUIT SUMMARY DESCRIPTION

Figure 3:
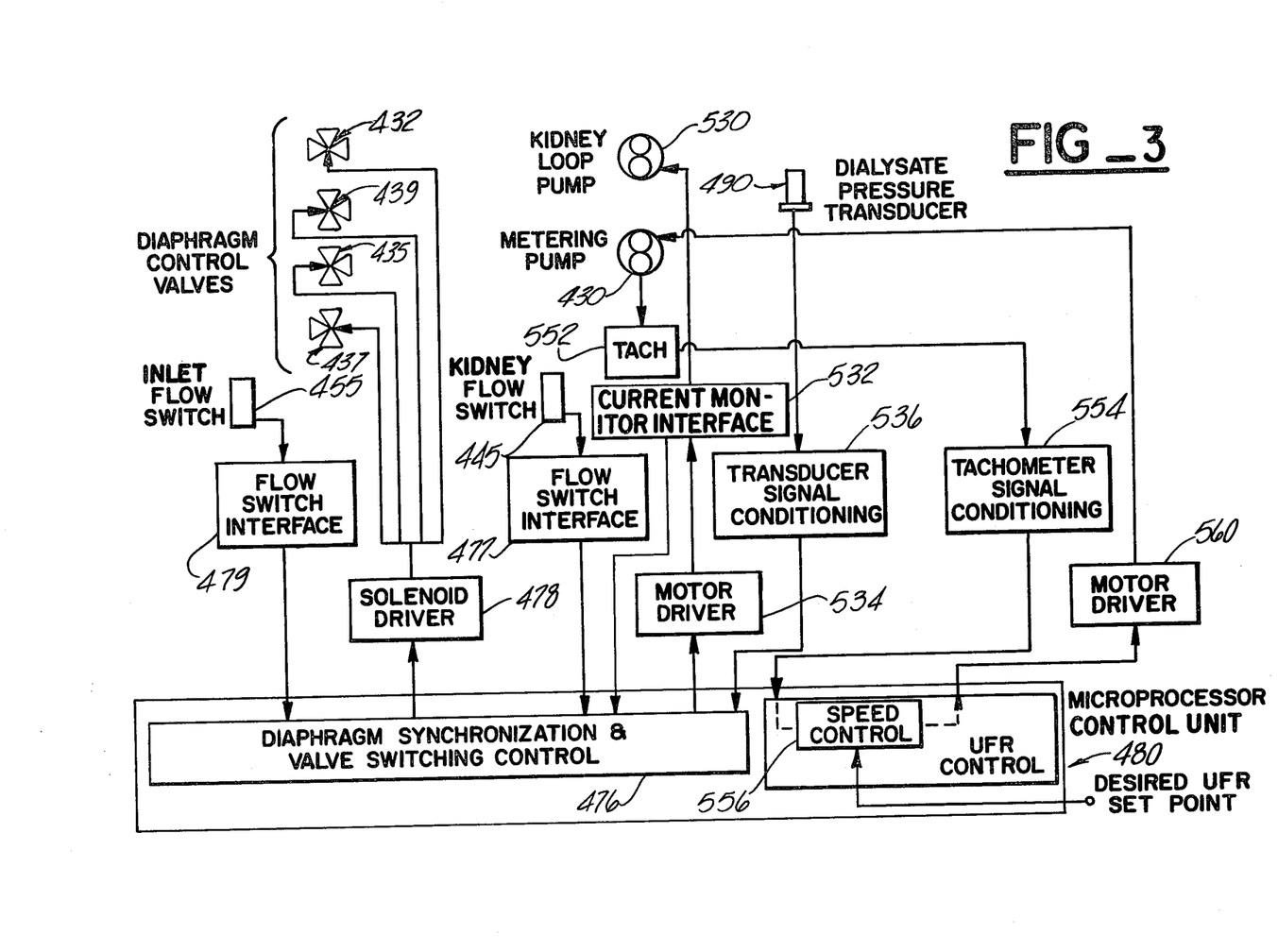
FIG. 3 is a block diagram representation of the interface connections between the operating elements of the circuit as shown in FIGS. 1 and 2 and the microprocessor control unit.

Referring to FIG. 3 the overall dialysate flow from cylinders 410 and 420 to and from artificial kidney 510 during valve states A and B, as above generally described, is effected automatically through electronic controls which function to monitor the flow rate of spent dialysate in line 470 and fresh dialysate in inlet line 450; kidney flow rate sensing means 445 in line 470 and inlet flow switch 455 in fresh dialysate supply line 450 detect the instant of end of stroke of diaphragms 407 and 407A in dialysate cylinders 410 and 420, respectively, on a continuous basis. These detected instants of diaphragm end of stroke are relayed to Microprocessor Control Unit, generally designated 480, and particularly to the Diaphragm Synchronization and Valve Switching Control Unit, 476, by electrical signals from Flow Switch Interface Units 447, 479. Control unit 476 is pre-programmed to activate Solenoid Driver 478 to reverse each of the valves 432, 435, 437 and 439 the instant the second of the two diaphragms 407 or 407A arrives at its end of stroke. Detection of diaphragm end of stroke may equally satisfactorily be performed by other means than flow rate sensing means 445 and 455 as will be readily understood by those skilled in the art. Satisfactory means include, for example, contact switches, pressure sensing means, optical sensors, fluidic sensing means associated with each cylinder, or the like.

Under perfect, or ideal steady-state, operating condition each of diaphragms 407 and 407A arrive at its end of stroke at the identical instant in time; normally, however, the instant of diaphragm end of stroke is not identical but rather is milli-seconds apart in time. The function of the control circuitry shown in FIG. 3 is to provide corrective electrical signals to means controlling the dialysate flow rate in spent dialysate line 470 to so change that flow rate, on an instantaneous basis, to synchronize the end of stroke of diaphragms 407, 407A in each half cycle of diaphragm traverse in cylinders 410, 420.

Kidney loop pump 530 is connected to Diaphragm Synchronization Control 476 through Motor Driver 534 and optionally present Current Monitor Interface 532 and its rate of operation is increased, or decreased, as required through ampere or voltage control, by Motor Driver 534, as will be more fully described in connection with the time sequence diagrams, FIGS. 7-14 inclusive. Dialysate Pressure Transducer 490 is interconnected to Diaphragm Synchronization Control 476 through Transducer Signal Conditioning unit 536; signals from transducer 490 are relayed substantially continuously, for example, at 50 millisecond intervals to indicate changes in pressure that effect flow rate through kidney loop pump 530. Diaphragm synchronization control 476, in response to the signal indicating pressure change activates the motor driver 534 to alter the rate of operation of pump 530 to counteract the flow rate change resulting from the pressure change and re-establish the flow rate to the level prior to the change in pressure.

Pump 430 is associated with tachometer 552 which relays the rate of pump 430 operation through Tachometer Signal Conditioning Unit 554 to Speed Control Means 556, a part of Microprocessor Control Unit 480; metering pump 430 is preset by the operator to the desired output rate for ultrafiltrate removal from the above atmospheric portion of the circuit by manual setting of the desired UFR Set Point. This setting is relayed by electrical signal through the Speed Control unit 556 which in turn activates Motor Driver 560, which feeds a control signal, which may be voltage or ampere regulation, to cause metering pump 430 to operate at the speed required to achieve the preset ultrafiltrate flow rate.

DETAILED DESCRIPTION OF DIAPHRAGM SYNCHRONIZATION OPERATION

Automatic operation of cylinders 410, 420 to alternately connect each with kidney 510 is intended to maintain a substantially constant rate of dialysate flow through the circuit. The objective of the control system is to react to changes in steady-state flow conditions at any point, or points, in the circuit which without correction would change the desired constant flow rate. The method employed is to detect the time difference between the instant of each end of stroke of each diaphragm and this is accomplished in the preferred embodiment of this invention by signals from flow switches 445 and 455 which are fed to control 476. Control 476 senses the incoming signals on a continuous basis and instantaneously converts the time difference into a correcting signal which varies the voltage to motor driver 534, as required, to change the flow rate in line 470 to equal the flow rate in line 450 when the diaphragms are next again moving in the same direction that they were moving to cause the detected time difference between the instant of end of strokes in that half cycle. While detection of time differences and the computation of the corrective voltage change occurs substantially instantaneously, the necessary synchronization of the rates of relative movement of the diaphragms requires a delay in applying that correction until the arrival of the next valve state which is the same valve state in which the difference first occurred, for example, valve state A. Thus, diaphragm synchronization control 476 detects the time difference but delays feeding the correcting signal to motor driver 534 until the beginning instant of the next succeeding half cycle during which flow is again occurring in valve state A. In normal operation traverse of the diaphragms occurs in about 13-15 seconds and a correcting signal applied to kidney pump 530 at the instant the valves switch from valve state B to valve state A has the full half-cycle to remain in effect and bring the flow rate in line 470 to the exact equal of that in line 450 by the end of that half cycle. Ordinarily, however, a single correction does not reestablish exact synchronization due to other changes that may occur at the other points in the circuit during the half cycle in which the correction is being applied and it is necessary to continuously detect time differences in the instants of diaphragm end of stroke, in both half cycles, and to constantly, and repeatedly, convert the detected time difference to corrective signals and to repetitively apply those signals, after delay, to the succeeding next half cycle of diaphragm operation. These principles of operation are illustrated in FIGS. 7-14 which show the control circuitry reaction and corrective action taken to overcome various types of flow rate changes which may occur during a hemodialysis treatment of 3 to 5 hours duration.

FIGS. 7-14 are time sequence diagrams. The variable time is plotted along the horizontal axis; the instantaneous condition of controlling circuit components and operating parameter levels which result from corrections to pump motor voltage to achieve diaphragm synchronization are plotted along the vertical axis. The diagrams show sequential half cycles in valve state A and valve state B and correlate on an instantaneous basis the status of Inlet Flow Switch 455 and Kidney Flow Switch 445 during each valve state. Flow switches are either "on" or "off" and the horizontal line plotted opposite each position shows the time duration of dialysate flow in that position for each of valve state A or B and the vertical lines indicate the instant of the end of each diaphragm stroke; the exact instant of the change from valve state A to valve state B is shown by the position of the vertical line plotted opposite the legend Valve State A or B.

Figure 7:
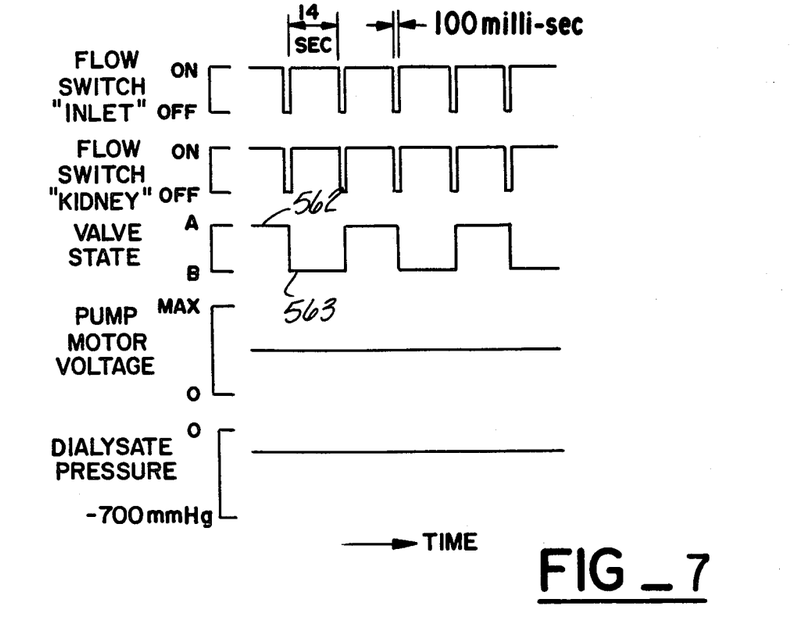
FIG. 7 is the time sequence diagram illustrating the relationship of the flow switches in the inlet, or fresh/drain loop, and in the kidney, or kidney/spent loop, to the pump motor voltage and to dialysate pressure as those switches reflect end of stroke in valve state A (FIG. 1) and valve state B (FIG. 2), and specifically illustrating steady state operation when the diaphragms in the two cylinders are in synchronization for both valve states A and B.

As may be seen in FIG. 7 the normal time elapse in each of Valve State A and B is 14 seconds and the normal time elapse during the change from one valve state to the other is approximately 100 milli-seconds. As there shown the width of the time elapse during valve switching is exaggerated to illustrate that both flow switches must reach their "off" position before the valves switch from valve state A to valve state B, and vice versa. By using the horizontal line 562 opposite Valve State A or line 563 opposite Valve State B as the control and extending an imaginary vertical line one can observe the instantaneous status of each of the inlet and kidney flow switches, and thus determine the time elapse for each switch to reach its off position. As shown in FIG. 7, the time elapse in Valve State A equals the time elapse in Valve State B and the diaphragms are reaching their end of stroke position at the same instant and are synchronized; the circuit is operating perfectly, and in ideal steady-state condition. In this mode no corrective changes are needed and the pump motor voltage and dialysate pressure remain steady.

Figure 8:
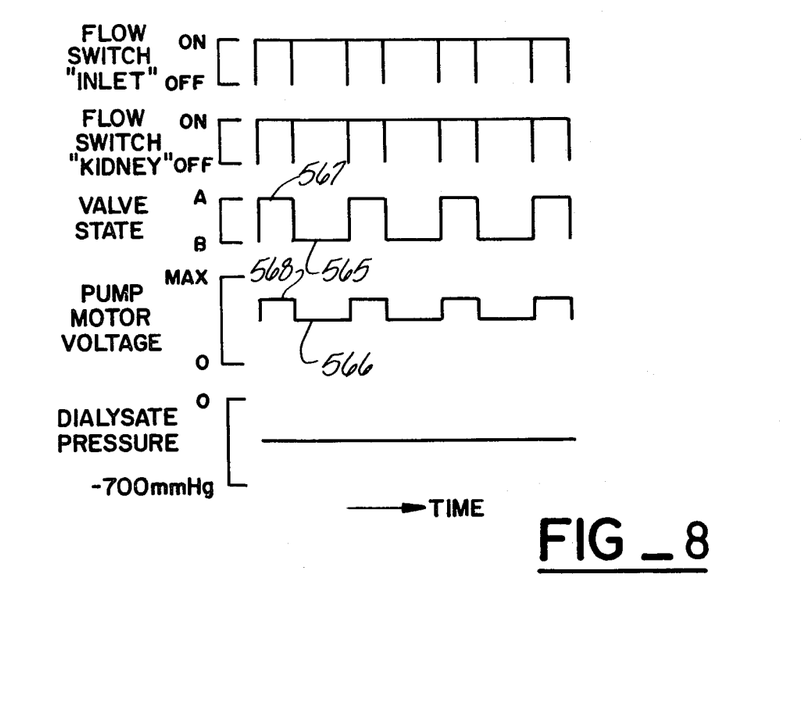
FIG. 8 is a time sequence diagram of the type shown in FIG. 7 which illustrates the operating condition of greater resistance to flow in the fresh/drain circuit in valve state B than in valve state A and specifically showing synchronized end of strokes of both diaphragms where the half-cycle time in valve state B exceeds that in valve state A.

In FIG. 8, another type of steady-state operation is illustrated. As may be seen, the rate of dialysate flow in valve state B is slower than during valve state A as indicated by the longer time elapse of line 565 relative to line 567; this reflects greater resistance to flow at some location within the circuit of FIG. 2 in the fresh/drain circuit. The slower rate of flow during valve state B is reflected by lower pump motor voltage as shown in line 566 relative to line 568; the inlet and kidney flow switches nevertheless reach their off positions at the same time instant in both of Valve States A and B and the diaphragms are synchronized because of the corrective signals to the pump 530.

Figure 9:
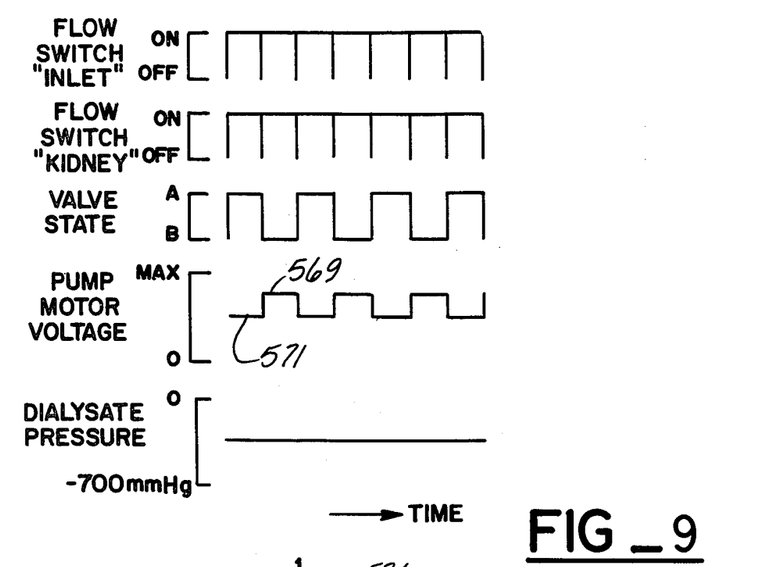
FIG. 9 is a time sequence diagram of the type shown in FIG. 7 which illustrates the operating condition of greater resistance to flow in the kidney/spent circuit in valve state B than in valve state A and equal resistance to flow in both valve states A and B in the fresh/drain circuit and specifically showing synchronized end of strokes of both diaphragms in equal half-cycle time periods resulting from the use of increased voltage to the pump means in the kidney/spent circuit during valve state B.

FIG. 9 illustrates a circuit condition in which there is greater resistance to dialysate flow in Valve State B at some location in the kidney/spent circuit than in the kidney/spent circuit in Valve State A. As shown, the pump motor voltage line 569 during Valve State B is higher than the pump motor voltage line 571 during Valve State A to overcome that greater resistance. During valve state B kidney pump 530 is supplied higher voltage sufficient to cause the flow rate in line 470 to equal that in line 450 so that the diaphragms are synchronized and operation is steady-state, as depicted.

Figure 10:
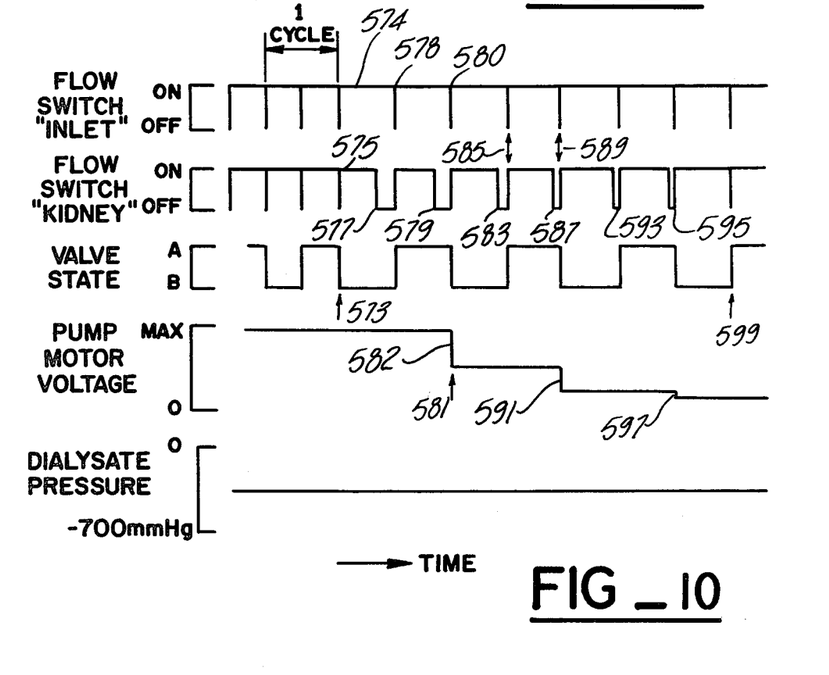
FIG. 10 is a time sequence diagram of the type shown in FIG. 7 which illustrates the operating condition resulting from a shift in incoming dialysate pressure in the fresh/drain circuit to a new lower level having a similar effect on both circuits in valve states A and B and specifically illustrating the half-cycle delayed adjustments made by the microprocessor to cause the kidney/spent circuit diaphragms to traverse their cylinders in the same elapsed time as the lengthened time required in the inlet or fresh/drain circuit such that the diaphragms become synchronized.

The circuit reaction to a drop in dialysate flow rate in inlet line 450 following a prior steady-state period of operation is illustrated on FIG. 10. Such a change could occur due to any external disturbance in the upstream dialysate generation circuit as, for example, a slow down of inlet dialysate pump 458 or the like. As may be seen in FIG. 10, two half-cycles in valve state A and one half cycle in valve state B were completed with the diaphragms in synchronization; a disturbance in the fresh/drain circuit occurred at the beginning of the half cycle in valve state B indicated at 573, and the inlet flow switch remained in its "on" position longer than in previous half-cycles which indicates an increased time of diaphragm traverse. This may be seen by comparing line 574 with kidney switch line 575. Kidney flow switch 445 signaled end of stroke of diaphragm 407 in cylinder 410 at its left hand extremity, FIG. 2, as indicated at 577 while diaphragm 407A remained in traverse until it reached its left hand extremity end of stroke as indicated at 578, at which time the valves switched to valve state A. A similar effect on diaphragm synchronization also occurred in the subsequent half-cycle Valve State A due to the inlet line flow rate decrease, and again kidney flow switch 445 signaled end of stroke of diaphragm 407A before diaphragm 407, FIG. 1, as may be seen by comparing points 579 and 580. These time differences are detected by control 476 and converted into corrective electrical signals for actuating motor driver 534. The first corrective signal, to correct the detected time difference in valve state B at instant 578 is applied one half-cycle later at the instant generally designated 581 which is the beginning of valve state B operation. The correction is an electrical signal which reduces pump motor voltage as shown by line 582. This correction reduced the time difference in valve state B by reducing the flow rate in line 470 thus causing kidney switch 455 to delay its operation at 583 relative to actuation of inlet switch 455 at instant 585. With the pump motor voltage remaining at its new lower level throughout valve state A, a similar reduction occurs in the actuation of kidney switch 445 at 587 relative to actuation of inlet switch at instant 589. A second reduction in pump motor voltage is applied at instant 589 as indicated at line 591, and during the succeeding half-cycles of valve state B and valve state A, a further decrease in the difference between the instants of ends of stroke occurred as shown at 593 and 595, and after a third correction of voltage at instant 595 as shown at line 597, synchronization was attained at instant 599 which is at the end of the third half-cycle in valve state B after the disturbance was first detected at instant 578.

Figure 11:
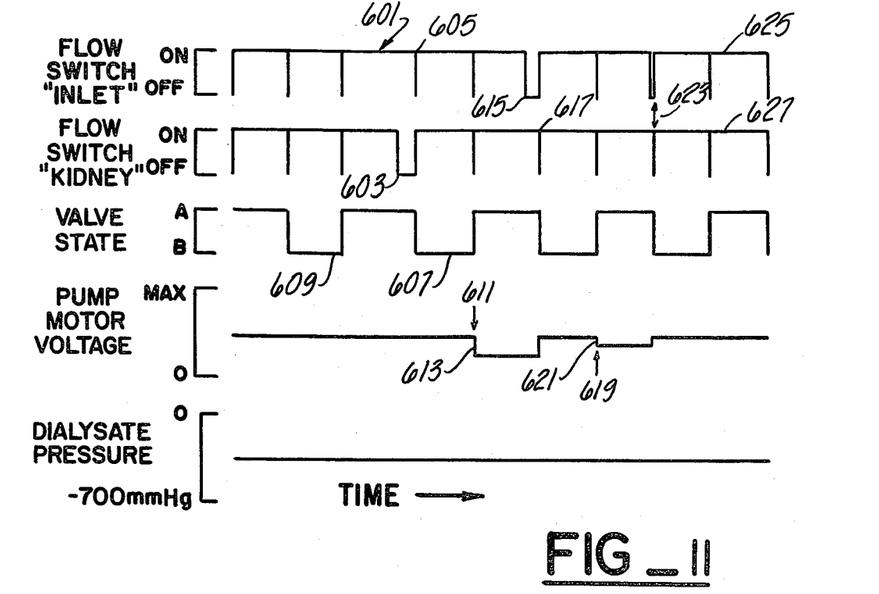
FIG. 11 is a time sequence diagram of the type shown in FIG. 7 which illustrates the operating conditions resulting from a momentary, single half-cycle reduced flow rate in the fresh/drain circuit in valve state A, only, and illustrating microprocessor corrections in succeeding, delayed half-cycles to re-establish diaphragm synchronization.

FIG. 11 illustrates a momentary reduction in dialysate flow rate in the fresh/drain circuit during valve state A which lasts for less than a complete half-cycle and does not continue into valve state B. As may be seen in FIG. 11 the reduced flow rate in valve state A occurs at instant 601 causing an earlier actuation of kidney switch 445 at instant 603 relative to actuation of inlet switch 455 at instant 605. The disturbance does not alter the flow rates in valve state B and the time elapse shown by line 607 following the disturbance is the same as the time elapse shown by line 609 prior to the disturbance. At instant 611, one half-cycle delayed after the time difference was detected at instant 605, a correction reducing pump motor voltage was made in the amount indicated by line 613. The correction caused too large a reduction in flow in line 470 during the corrected half-cycle in valve state A, as reflected by the early actuation of flow switch 455 at instant 615 prior to kidney switch 455 at instant 617. This over-correction was offset on the succeeding half-cycle in valve state A at instant 619 by a smaller voltage reduction as indicated by line 621, and this correction reduced the amount of early actuation of inlet switch 455 relative to kidney flow switch 445 as indicated at instant 623, and thereafter synchronization was achieved in the succeeding valve state A half-cycle as may be seen by comparing line 625 and line 627.

Figure 12:
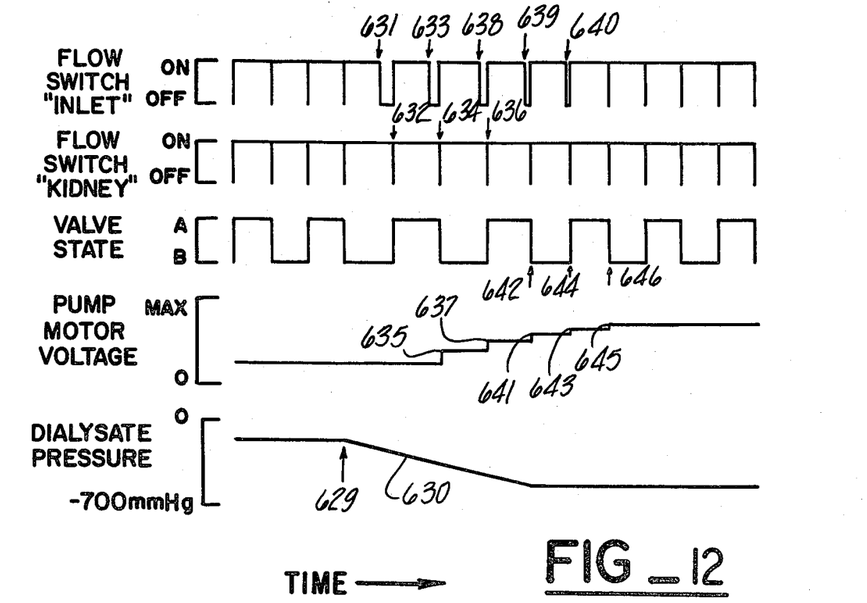
FIG. 12 is a time sequence diagram of the type shown in FIG. 7 which illustrates the operating condition resulting from an operator setting of higher ultrafiltrate withdrawal rate and specifically illustrating the successive changes in pump motor voltage to achieve synchronization at a numerically greater negative pressure across the semipermeable membrane through detected differences in end of stroke of the diaphragms.
Figure 13:
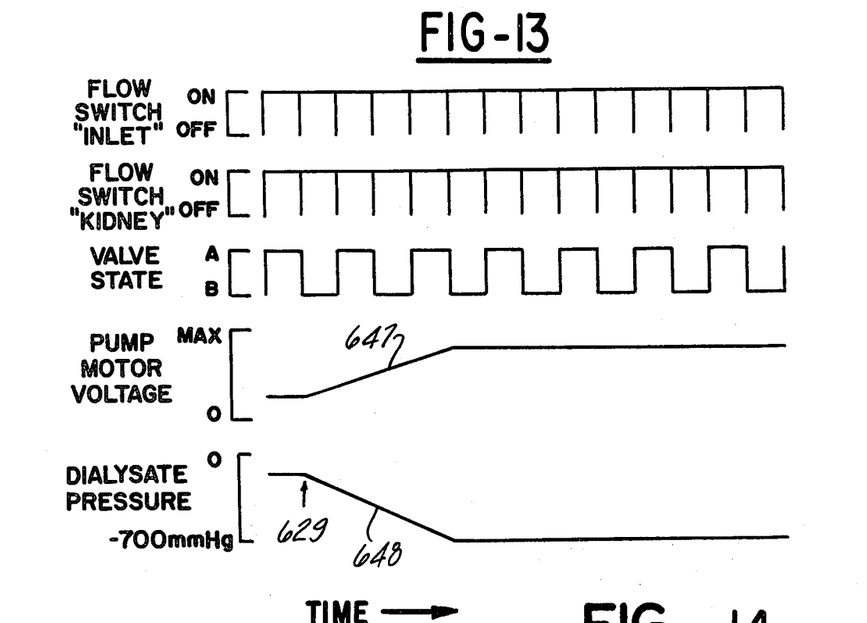
FIG. 13 is a time sequence diagram of the type shown in FIG. 12 and illustrating the effect of optional inclusion in the circuit of a pressure transducer which continuously monitors dialysate pressure changes in the low pressure lines and changes pump voltage to compensate for pressure-induced changes in pump output independently of voltage changes dictated by detected differences in the instant of the end of stroke of the two diaphragms.

In FIGS. 12 and 13 the effect of operator change during the hemodialysis treatment to increase the rate of ultrafiltrate withdrawal is illustrated. FIG. 12 shows automatic adjustment to counteract the change in UFR withdrawal rate when the circuit employs the preferred gear pump 530, or its equivalent, and does not include the optionally present dialysate pressure transducer 490. FIG. 13 illustrates control circuit operation to the same change in UFR withdrawal rate in the same circuit except that pressure transducer 490 is present in the circuit. As shown in FIGS. 12 and 13, the operator increases the UFR withdrawal rate at instant 629; to produce the demanded increase in ultrafiltrate the closed, hydraulic tight, bubble-free dialysate flow circuit causes the dialysate pressure to decrease, gradually as indicated by the uniformly sloping line 630. In the valve state B half-cycle after the UFR increase the inlet flow switch closes at instant 631 earlier than the kidney flow switch at instant 632, and in the succeeding valve state A half-cycle inlet switch 455 again closes early at instant 633 relative to kidney flow switch 445 as the dialysate pressure continues to gradually decrease. At the beginning of the next valve state B half-cycle after the early closure at instant 631 an upward voltage correction 635 is made at instant 634 to increase the speed of kidney pump 530 as an offset to the effect that the dialysate pressure drop has on the gear pump output. A similar upward correction in pump motor voltage is made at instant 636 at the beginning of the valve state A half-cycle as indicated at 637 to correct the early closure at instant 633. The gradual dialysate pressure decrease continues to cause early closures of the inlet flow switch 455 at instant 638 in valve state B, at instant 639 in valve state A and at instant 640 in valve state B. An upward pump motor voltage correction 641 is made at instant 642 to offset the early closure at instant 638; another upward correction 643 is made at instant 644 at the beginning of valve state A to offset the early closure at instant 639. Another correction 645 is made at instant 646 to offset the early closure in valve state B at instant 640 and thereafter the diaphragms are in synchronization and operating in steady-state at the increased ultrafiltrate withdrawal rate set 84 seconds earlier at instant 629.

In contrast to the five successive corrections to pump motor voltage to again attain synchronization as shown in FIG. 12, the presence of pressure transducer 490 in the circuit assures continuation of synchronization during all pressure changes in kidney 510. Pressure transducer 490 functions by monitoring pressure changes in spent dialysate line 470 at 50 milli-second intervals and sends an electrical signal generated by Transducer Signal Conditioning Unit 536 to Diaphragm Synchronization Control 476. Control 476, pre-programmed to initiate kidney pump voltage corrections to offset such pressure changes, signals through Motor Driver 534 a small voltage increase to cause kidney pump 530 to speed up slightly and restore the flow rate through pump 530 to that existing prior to the pressure change detected by pressure transducer 490. Successive 50 milli-second spaced monitoring signals produce similar small corrections. As shown in FIG. 13 pump motor voltage is gradually and smoothly increased along line 647 after the ultrafiltrate withdrawal rate was increased at instant 629 and dialysate pressure gradually reached the same lower pressure level along line 648 that was reached in the operation of the circuit without transducer 490 as shown in FIG. 12. Throughout the small voltage corrections in FIG. 13 the diaphragms remained in synchronization and all voltage corrections were completed in four half-cycles or in 56 seconds and terminated substantially at the same instant the new lower pressure was reached in kidney 510.

Figure 14:
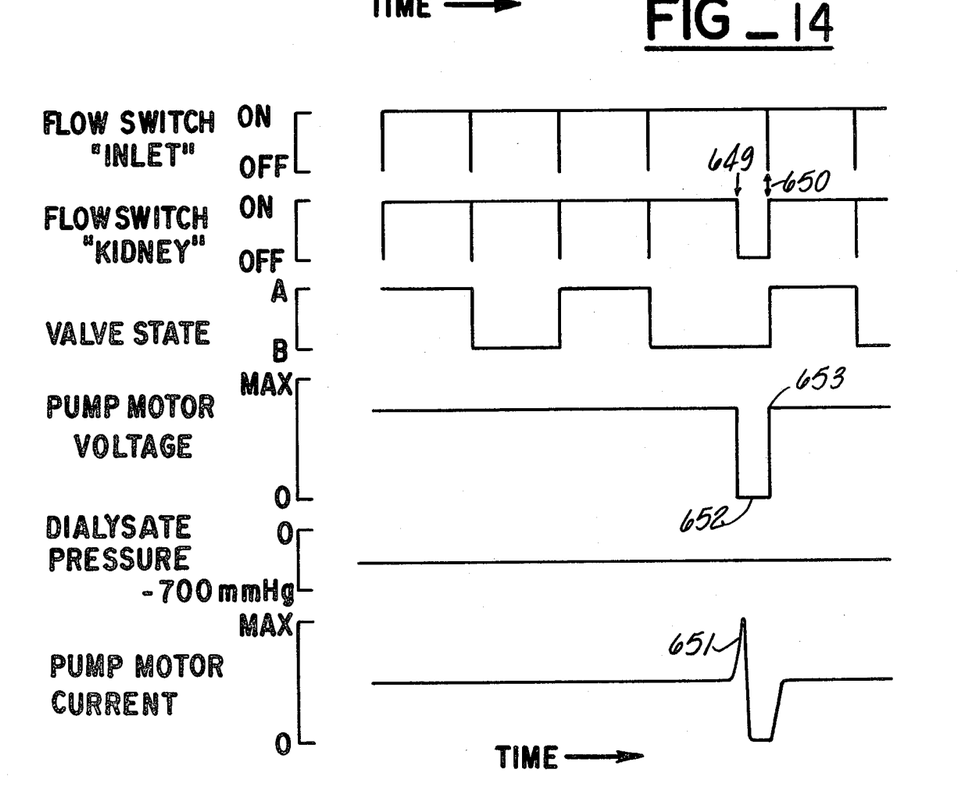
FIG. 14 is a time sequence diagram of the type shown in FIG. 7 which illustrates an embodiment of the invention insuring safe operation of the circuit during the period of no flow of the fluid in the spent dialysate removal line due to diaphragm arrival at end of stroke in that line prior to arrival at end of stroke of the diaphragm in the fresh/drain circuit in either valve state A or B.

FIG. 14 illustrates an embodiment of the invention which is operative when optionally present Current Monitor Interface 532 is present in the circuit. Current Monitor Interface 532 monitors the slope of the line determined by current as a function of time. Interface 532 is useful in a circuit that employs a pump driven by a direct current permanent magnet motor. In such motors the current draw is proportional to output load and in the event flow becomes blocked in the output line the current rises sharply. Such output line blockage does occur each time the diaphragm in the kidney/spent circuit reaches its end of stroke before the diaphragm in the fresh/drain circuit arrives at its end of stroke. In that interim, pump 530 continues to receive its normal operating voltage and continues to pump toward the diaphragm in the now filled kidney/spent cylinder such that pressure rapidly increases in the circuit elements between the outlet of pump 530 and the outlet of the cylinder in the kidney/spent circuit which includes bubble trap 440, flow switch 445 and the valves. Such pressure increases may cause rupture of valve seals, or puncture the diaphragm or disable the exit vent on trap 440 and should therefore be avoided. In FIG. 14, the automatic control circuit response to such an event is shown. After three half-cycles of steady-state operation an event occurs such as a momentary reduction in the flow in the fresh/drain circuit which causes the diaphragm in the kidney/spent line to arrive first at its end of stroke and to activate flow switch 445 in the kidney/spent circuit as shown at instant 649 prior to actuation of inlet flow switch 455 at instant 650. In the interim between instants 649 and 650, for example, 1 to 2 seconds, pump current rises sharply as shown at 651 and relay of this steep rise to the Diaphragm Synchronization control 476 from Current Monitor Interface 532 causes a preprogrammed electrical signal from control 476 through Motor Driver 534 to drop the Pump Motor voltage to zero as shown at 652. At time instant 650 when the valves switch to valve state A the normal voltage is restored to pump 530 as shown at 653.

What is claimed is:

1. An automated single pass negative pressure dialysate hemodialysis treatment circuit for automatically controlling hemodialyzer and dialysate operating parameters in response to operator set ultrafiltrate withdrawal rate comprising:

a hemodialyzer separated by a semipermeable membrane into a blood side and a dialysate side having inlet and outlet ports for removing water and impurities from the blood;

a first dialysate cylinder having hydraulically driven means separating said cylinder into two chambers as said means moves between the ends of said cylinder connected to a fresh/drain circuit for filling one of said chambers via a dialysate supply line with fresh dialysate as spent dialysate is removed from the other of said chambers to drain via a drain line and alternately connected to a kidney/spent circuit for filling one of said chambers with spent dialysate via a kidney spent dialysate removal line as fresh dialysate is removed from the other of said chambers and supplied to the inlet port of said kidney via a kidney dialysate supply line;

a second dialysate cylinder having hydraulically driven means separating said cylinder into two chambers as said means moves between the ends of said cylinder connected to said kidney/spent circuit during the time said first cylinder is connected to said fresh/drain circuit and alternately connected to said fresh/drain circuit during the time said first cylinder is connected to said kidney/spent circuit;

valve switching means associated with said first and said second cylinders connecting said cylinders alternately with one of said fresh/drain and said kidney/spent circuits;

dialysate flow control means connected into said kidney spent dialysate removal line intermediate said kidney dialysate outlet port and said valve switching means for controlling the rate of spent dialysate flow in said kidney spent dialysate removal line, a degasifier connected into said kidney spent dialysate removal line intermediate said pump and said valve switching means in said kidney/spent circuit;

ultrafiltrate removal means connected into an above atmospheric portion of said circuit intermediate said valve switching means and means in said kidney dialysate supply line and means in said spent dialysate removal line which preserve said above atmospheric pressure in said above atmospheric circuit portion, and means for setting the rate of withdrawal of ultrafiltrate from said portion of said circuit;

sensing means for sensing the end of stroke of said hydraulically driven means in each of said first and said second cylinders and for converting said sensed instant into an electrical signal;

means for causing said valve switching means to simultaneously switch all valves controlling flow into and from each of said first and said second cylinders at the instant of arrival of the end of stroke of the second of said hydraulically driven means in said first and said second cylinders for alternating the existing connection of each of said cylinders with one of said fresh/drain and said kidney/spent circuits;

detecting means operatively connected to said electrical signal of said end of stroke sensing means for detecting the time difference between the instant of each said end of stroke of each of said hydraulically driven means and for converting said time difference into a flow rate electrical signal for supply to said pump means for altering the flow rate of said spent dialysate in said kidney spent dialysate removal line, flow rate signal generator means for supplying to said pump means said flow rate signal at the delayed instant of the end of the succeeding half cycle of traverse to the same end of stroke from which the said detected time difference first occurred for causing said pump to adjust the rate of dialysate flow in said kidney spent dialysate removal line to thereby achieve synchronization of the instant of end of stroke of each of said hydraulically driven means in said cylinders.

2. An automated hemodialysis treatment circuit in accordance with claim 1 wherein said hemodialyzer is a hollow fiber artificial kidney.

3. An automated hemodialysis treatment circuit in accordance with claim 1 wherein said circuit includes pressure sensing means in said spent dialysate removal line intermediate said pump and said outlet hemodialyzer port for sensing pressure changes in spent dialysate in said kidney/spent dialysate removal line and for converting said pressure change into an electrical signal for supply to said pump means to re-establish the rate of dialysate flow through said pump means at the instant prior to said detected change in said pressure.

4. An automated hemodialysis treatment circuit in accordance with claim 1 wherein said circuit includes a first sensing means consisting of a flow switch intermediate said fresh dialysate source and said valve switching means in said fresh dialysate supply line, and a second sensing means consisting of a flow switch in said kidney/spent circuit intermediate said pump and said valve switching means in said spent dialysate removal line.

5. An automated hemodialysis treatment circuit in accordance with claim 4 wherein said circuit includes pump means in said fresh/drain circuit intermediate said fresh dialysate source and upstream of said valve switching means in said fresh dialysate supply line.

6. An automated hemodialysis treatment circuit in accordance with claim 1 wherein said hydraulically driven means is a diaphragm.

7. A process for conducting a hemodialysis treatment by employing a hemodialyzer in a closed hydraulic circuit including dialysate delivery means arranged such that operator presetting of the rate of withdrawal of ultrafiltrate from said circuit induces automatically those operating parameters in the circuit which produce water removal from the blood so as to insure maintenance of the rate of water separation across the semipermeable membrane to enable continuous withdrawal of ultrafiltrate at the preset withdrawal rate comprising the steps of:

providing a closed hydraulic circuit including a first and second cylinder unit, each having hydraulically driven means separating each said cylinder into two chambers as said means moves between the ends of said cylinder, a hemodialyzer separated by a semipermeable membrane into a blood side and a dialysate side having an inlet port and an outlet port, switching means operatively connecting one of said units with said hemodialyzer and the other said unit with a fresh dialysate supply source on an alternating time basis such that one chamber in said first cylinder unit fills with fresh dialysates as spent dialysate is expelled from the other chamber in said unit to drain, and during that same time interval the other of said units is connected to said hemodialyzer such that one chamber in said second cylinder unit fills with spent dialysate as fresh dialysate is expelled from the other chamber in said unit to the inlet port of said hemodialyzer and said functions alternate after simultaneous valve switching occurs, fresh dialysate supply line means in said hydraulic circuit for supplying bubble-free fresh dialysate and spent dialysate line means for removing gas bubbles from said spent dialysate before said degasified spent dialysate enters a chamber in one of said first and said second cylinder unit, and presettable means in said circuit interconnecting said hemodialyzer with one of said first and said second cylinder units for withdrawing ultrafiltrate therefrom, sensing the end of stroke of each said hydraulically driven means in each of said first and said second cylinder, switching all valves controlling flow into and from each of said first and said second cylinders simultaneously at the instant of latest arrival of the end of stroke of said hydraulically driven means in said first and said second cylinders to thereby alternate connection between each of said cylinders and one of said fresh/drain and said kidney/spent circuits, detecting the time difference between the instant of each end of stroke of each of said hydraulically driven means, converting said detected time difference into a flow rate electrical signal, supplying said flow rate electrical signal to pump means located in said spent dialysate line at the delayed instant of the end of the succeeding half cycle of traverse to the same end of stroke location from which the said detected time difference first occurred, and repeating said time difference detection between the instant of said end of strokes of said hydraulically driven means in each said cylinder in subsequent cycles and after conversion of said time difference into flow control signals again supplying said signals to said pump means at similarly delayed instants in time for a sufficient number of half cycles to achieve synchronization of the instant of end of stroke of each of said hydraulically driven means in said cylinders.

8. A process in accordance with claim 7 wherein pressure changes in said spent dialysate in said spent dialysate removal line intermediate said pump and said outlet hemodialyzer port are sensed and converted into electrical signals and supplied to said pump means on a repetitive, continuous basis to thereby re-establish the rate of dialysate flow through said pump means at the instant prior to said sensed change in said pressure.

* * * * *